US008268594B2

(12) United States Patent
Martin et al.

(10) Patent No.: US 8,268,594 B2
(45) Date of Patent: Sep. 18, 2012

(54) **PYRC AS A SELECTION MARKER IN *ESCHERICHIA COLI***

(75) Inventors: Franck Martin, L'Aquila (IT); Stefano Cencioni, L'Aquila (IT); Antonella Colagrande, L'Aquila (IT); Maria Cristina Thaller, Rome (IT); Marco Maria D'Andrea, Siena (IT); Gian Maria Rossolini, Siena (IT)

(73) Assignee: Advanced Accelerator Applications S.A., Saint Genis Pouilly (FR)

( * ) Notice: Subject to any disclaimer, the term of this patent is extended or adjusted under 35 U.S.C. 154(b) by 326 days.

(21) Appl. No.: 12/083,088

(22) PCT Filed: Oct. 4, 2006

(86) PCT No.: PCT/EP2006/067053
§ 371 (c)(1),
(2), (4) Date: Apr. 23, 2010

(87) PCT Pub. No.: WO2007/039632
PCT Pub. Date: Apr. 12, 2007

(65) Prior Publication Data
US 2010/0216190 A1    Aug. 26, 2010

(30) Foreign Application Priority Data
Oct. 6, 2005 (EP) .................................... 05109274

(51) Int. Cl.
*C12P 21/04* (2006.01)
*C12P 21/06* (2006.01)
*C12N 1/12* (2006.01)
*C12N 1/20* (2006.01)
*C12N 15/00* (2006.01)

(52) U.S. Cl. .................. 435/71.1; 435/69.1; 435/252.1; 435/252.33; 435/320.1

(58) Field of Classification Search .................. None
See application file for complete search history.

(56) References Cited

U.S. PATENT DOCUMENTS
2005/0186666 A1* 8/2005 Schneider et al. ............ 435/108

FOREIGN PATENT DOCUMENTS
EP    0 972 838 A1    1/2000
JP    2000/050888    2/2000

OTHER PUBLICATIONS

Wilson et al., J. Bacteriol. 169:3051-3058, 1987.*
pUC18, C19 Plasmid Map, May 15, 2000, obtained from dwb4.unl.edu/Chem/CHEM869N/CHEM869NLinks/www.fermentas.com/techinfo/NucleicAcids/mappuc1819.htm, last viewed on Feb. 10, 2011, 2 pages.*
Jensen et al., Eur. J. Biochem. 140:343-352, 1984.*
Bäckström et al., Eur. J. Biochem. 160:77-82, 1986.*
GenBank Accession No. L09136, Apr. 1993, 2 pages.*
Queen et al., Proc. Natl. Acad. Sci. USA, 86:10029-10033, 1989.*
GenBank Accession No. J01749, Jun. 2002, 6 pages.*
Weidner et al., Appl. Environmen. Microbiol. 766-771, 1996.*
Vasantha et al., J. Bacteriol. 158:884-889, 1984.*
Schneider et al., "Auxotrophic Markers *pyrF* and *proC* Can Replace Antibiotic Markers on Protein Production Plasmids in High-Cell-Density *Pseudomonas fluorescens* Fermentation," Biotechnol. Prog., vol. 21, 2005, pp. 343-348.
Cereghino et al., "New selectable marker/auxotrophic host strain combinations for molecular genetic manipulation of *Pichia pastoris*," Gene, vol. 263, 2001, pp. 159-169.
Schenk-Groninger et al., "Cloning, sequencing, and characterizing the *Lactobacillus leichmannii pyrC* gene encoding dihydroorotase," Biochimie, vol. 77, 1995, pp. 265-272.
Wilson et al., "Translational Control of *pyrC* Expression Mediated by Nucleotide-Sensitive Selection of Transcriptional Start Sites in *Escherichia coli*," Journal of Bacteriology, vol. 174, No. 2, 1992, pp. 514-524.
Degryse, "Stability of a host-vector system based on complementation of an essential gene in *Excherichia coli*," vol. 18, 1991, pp. 29-40.
Cranenburgh et al., "*Escherichia coli* strains that allow antibiotic-free plasmid selection and maintenance by repressor titration," Nucleic Acids Research, vol. 29, No. 5, 2001, pp. 1-6.
Fiedler et al., "*pro*BA complementation of an auxotrophic *E. coli* strain improves plasmid stability and expression yield during fermenter production of a recombinant antibody fragment," Gene, vol. 274, 2001, pp. 111-118.
Datsenko et al., "One-step inactivation of chromosomal genes in *Excherichia coli* K-12 using PCR products," PNAS, vol. 97, No. 12, 2000, pp. 6540-6545.
Hoffman, B. et al., Lactose fed-batch overexpression of recombinant metalloproteins in *Escherichia coli* BL21(DE3): process control yielding high levels of metal-incorporated, soluble protein, Proto Exp. Purif., 1995, vol. 6, pp. 646-654.
Murphy, D.B. et al., Guidance for Industry. Guidance for Human Somatic Cell Therapy and Gene Therapy. Food and Drug Administration, 1998, Rockville, M.D.
Gerdes, K. et al., Translational control and differential RNA decay are key elements regulating postsegregational expression of the kiler protein encoded by the parB locus of plasmid R1, Sep. 5, 1988, J. Mol. Biol., vol. 203, pp. 119-129.

(Continued)

*Primary Examiner* — David J Steadman
(74) *Attorney, Agent, or Firm* — Steinfl & Bruno, LLP

(57) ABSTRACT

The present invention relates to a method of producing a recombinant protein comprising using a selection method other than antibiotics. In particular, it relates to a stable host/vector system based on the pyrC gene complementation designed to produce high level of heterologous recombinant protein in *Escherichia coli*.

The expression system of the present invention allows rapid selection of plasmid containing cells during the cloning phases and lead to high protein expression during fermentation. This system has a strong selective efficiency, especially during the induction phase, leading to the selection of an almost homogeneous and stable plasmid bearing cell population. Moreover the productivity of the culture is to a large extent better than the one based on antibiotic resistance.
This elevated vector stability combined with its high productivity fulfils the requirements for heterologous protein production in *Escherichia coli* to an industrial level.

12 Claims, 5 Drawing Sheets

OTHER PUBLICATIONS

Pecota, D.C. et al., Antimicrobial properties of the *Escherichia coli* R1 plasmid host killing peptide, J. Biotechnol., Jan. 9, 2003, vol. 100, issue 1, pp. 1-12.

Bullock, W.O. et al., XII-Blue, a high efficiency plasmid transforming *recA Escherichia coli* strain with beta galactosidase selection, Biotechniques, 1987, vol. 5, pp. 376-378.

Yanisch-Perron, C. et al., Improved M13 phage cloning vectors and host strains: nucleotide sequences of the M13mp18 and pUC19 vectors, *Gene*, 1985, vol. 33, pp. 103-119.

Backstrom, D. et al., Nucleotide sequence of the structural gene for dihydroorotase of *Escherichia coli* K12, *Eur. J. Biochem.*, Oct. 1, 1986, vol. 160, issue 1, pp. 77-82.

Figini, M. et al., Panning phage antibody libraries on cells: isolation of human Fab fragments against ovarian carcinoma using guided selection, *Cancer Res.*, Mar. 1, 1998, vol. 58, issue 5, pp. 991-996.

Duenas, M. et al., Intra- and extracellular expression of an scFv antibody fragment in *E. coli*: effect of bacterial strains and pathway engineering using GroES/L chaperonins, Biotechniques, Mar. 1994, vol. 16, issue 3, pp. 476-477,480-483.

Gallagher, C.N. et al., Studies of the M15 beta-galactosidase complementation process, J. Protein Chem., Feb. 1998, vol. 17, issue 2, pp. 131-141.

Langley, K.E. et al., beta-Galactosidase alpha complementation: properties of the complemented enzymes and mechanism of the complementation reaction, Biochemistry, Nov. 2, 1976, vol. 15, issue 2, pp. 4866-4875.

Sato, T. et al., Genetic studies of an *Escherichia coli* K-12 temperature-sensitive mutant defective in membrane protein synthesis, J. Bacteriol., May 1979, vol. 138, issue 2, pp. 305-313.

Larsen, I.N., et al., Nucleotide sequence of the pyrD gene of *Escherichia coli* and characterization of the flavoprotein dihydroorotate dehydrogenase, Eur. J. Biochem., Aug. 15, 1985, vol. 151, issue 1, pp. 59-65.

Summers, D.K. et al., Multimerization of high copy number plasmids causes instability:ColE 1 encodes a determinant essential for plasmid monomerization and stability, *Cell*, Apr. 1984, vol. 36, issue 4, pp. 1097-1103.

Porter R.D. et al., The single-stranded-DNA-binding protein encoded by the *Escherichia coli* F factor can complement a deletion of the chromosomal ssb gene, *J. Bacteriol.*, Apr. 1991, vol. 173, issue 8, pp. 2720-2723.

Laemmli, U.K., Cleavage of structural proteins during the assembly of the head of bacteriophage T4, Nature, Aug. 15, 1970, vol. 277, pp. 680-685.

Towbin, R. et al., Electrophoretic transfer of proteins from polyacrylamide gels to nitrocellulose sheets, Proc. Natl. Acad. Sci. USA, Sep. 1979, vol. 76, pp. 4350-4354.

Banks G.R. et al., Cloning of the *PYR3* Gene of *Ustilago maydis* and Its Use in DNA Transformation, Molecular and Cellular Biology, Dec. 1988, pp. 5417-5424.

International Search Report issued for PCT/EP2006/067053 filed on Oct. 4, 2006 in the name of DOMPE PHA.R.MA s.p.a.; mail date: Mar. 7, 2007.

Written Opinion issued for PCT/EP2006/067053 filed on Oct. 4, 2006 in the name of DOMPE PHA.R.MA s.p.a.; mail date: Mar. 7, 2007.

* cited by examiner

PYRC AS A SELECTION MARKER IN *ESCHERICHIA COLI*

BRIEF DESCRIPTION OF THE INVENTION

The present invention relates to a method of producing a recombinant protein comprising using a selection method other than antibiotics. In particular, it relates to a stable host/vector system based on the pyrC gene complementation designed to produce high level of heterologous recombinant protein in *Escherichia coli*.

STATE OF THE ART

Heterologous protein expression systems commonly use plasmids to clone and express genes of interest in microorganisms. When these autonomously replicating DNA fragments are used as protein expression vectors their design is always based on i) an origin of replication to ensure autonomous replication; ii) a promoter to drive the transcription of the gene of interest; and iii) a selection gene to ease the selection of plasmid bearing cells.

Selection genes usually encode enzymes conferring resistance to antibiotics, which are used during the cloning steps and culture growth. During cloning, the presence of an antibiotic in the plates allows selection of the cells which have incorporated the plasmid during transformation, rendering the identification of recombinant colony forming units (cfu) easier. In the case of liquid culture growth, addition of the appropriate antibiotic in the culture broth, will prevent plasmid loss and keep the cell population homogeneous. Over time the expression vector is lost as the overall metabolic charge of the microorganism favours plasmidless cell growth. This decreases the recombinant protein expression yield. Therefore, having an homogeneous culture, in which every cell will host an expression vector is very important to obtain elevated production of the recombinant protein. The progressive dilution of the recombinant protein producing microorganisms will lead to the "dilution" of the recombinant protein into the host. This phenomenon is amplified further if the culture broth is a poor medium, such as a synthetic one, in which the microorganism will have to synthesize the majority of its metabolites.

In order to prevent plasmid loss, a selective pressure, such as that deriving from the use of an antibiotic, is usually added to the culture medium, where the gene coding for the resistance is cloned into the expression vector. The most common system uses ampicillin and the related β-lactamase gene whose product hydrolyses the antibiotic present in the medium. This type of mechanism of action leads to the progressive disappearance of ampicillin in the medium as culture goes on and cell number increases. Since ampicillin is a bacteriostatic drug, plasmidfree cells (i.e. untransformed cells) will start to proliferate as soon as the remaining antibiotic concentration is permissive. This phenomenon of delayed growth is particularly visible on plates, where after a while, around the major colony forming units (cfu) so called "satellites" start to grow.

To thwart the delayed growth of untransformed cells and therefore obtain a major culture homogeneity, the ampicillin concentration can be increased in the preculture [1] or replaced by bactericidal compounds, such as kanamycin or tetracycline. Kanamycin interacts with the 30 s ribosome complex and prevents the initiation of protein translation. Tetracycline acts on the same target and blocks the addition of new amino acids during polypeptide synthesis. This latter strategy works quite well and has a higher propensity to stabilize the presence of the expression vector in the cell.

Unfortunately these expression vector stabilization approaches cannot be used for producing proteins for human therapy according to protocols of Good Manufacturing Practice (GMP). For example, Ampicillin is excluded in these protocols due to allergenicity problems, whereas for other antibiotics validation is required to demonstrate the elimination of the antibiotics during the purification process [2]. Another point to consider is the demonstration of construct stability during cell culture over the generations. Consequently plasmid stabilization systems other than drug resistances are still highly desired.

A natural mechanism of plasmid stabilization by post-segregational killing of plasmid free cells by the hoc/sok system has already been reported in literature [3]. The hok gene product is a potent cell-killing protein whereas the sok gene encodes a small anti-sense RNA complementary to the hok mRNA. Both genes are located on the plasmid and are transcribed in the opposite directions. The hok mRNA is extraordinarily stable (hours), while the sok RNA decays rapidly (less than 30 s). In cells that have lost the plasmid, the stable transcript hok mRNA remains and its product kills the cell by membrane depolarization in the absence of the unstable sok RNA [4].

Natural plasmid loss in the absence of selective pressure is difficult to minimise and therefore a new system of vector stabilization not based on antibiotic selective pressure which is GMP compliant is required.

Expression vector stability is an important issue when recombinant protein production is carried out in a prokaryotic host, such as *Escherichia coli*, where plasmids remain episomal and therefore have an independent segregation mechanism as compared to the bacterial chromosome. Stable expression vectors are needed since the overall yield of recombinant protein production will depend on the plasmid presence which in turn is dependant on the capacity of the microorganism to maintain it (metabolic load). At the laboratory level the problem of plasmid loss can be circumvented by addition of an antibiotic in the culture medium which will force the bacteria to maintain the plasmid encoding for the antibiotic resistance and consequently the gene of interest. In contrast, when protein production for human use has to be carried out according to GMP, the presence of an antibiotic in the culture medium is not acceptable. Nevertheless, in order to start culture with an homogeneous population, a selective pressure is absolutely necessary to isolate plasmid bearing bacteria. Furthermore, during cell culture, the selective pressure will prevent the growth of plasmidfree cells, which only produce host proteins and can be considered as unwanted "contaminants". Until now antibiotic selection was being used during Master and Working cell banks realization, while, starting from an homogeneous population, the antibiotic was omitted during cell culture thus allowing plasmid escape. Therefore it would be convenient to develop a system, not based on antibiotic resistance to maintain a selective pressure during the whole process.

DETAILED DESCRIPTION OF THE INVENTION

Figure 1:
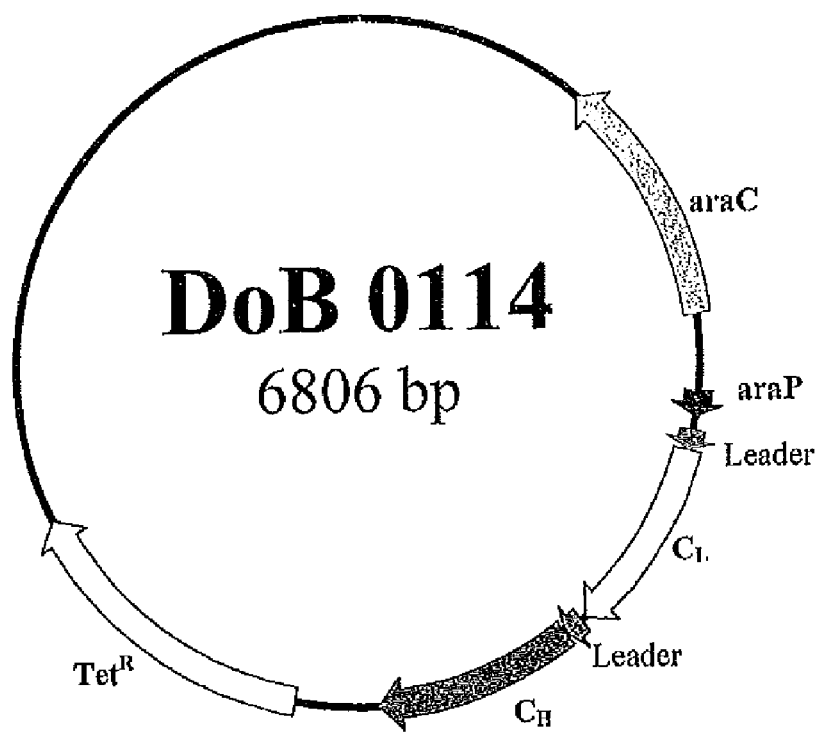
FIG. 1 Map of DoB 0114 expression vector based on Tet selection resistance.

Based on the above considerations we have developed a novel selection system suitable for GMP production and based on a host/vector couple in which the microorganism growth is strictly dependent on the plasmid presence in a selective minimal medium. A minimum medium is advantageous for protein production for human use, since it does not contain for example BSE or GMOs from various sources. Another advantage is the low foaming tendency of those media which favour oxygen transfer rate and the possibility to impose the carbon source for the microorganism growth. Since *Escherichia coli* metabolism has been deeply characterized, numerous strains are available and among them one can choose the best strain for this complementation experiment in consideration of the available or desired carbon source.

In a first attempt the β-galactosidase enzyme had been identified as the candidate of choice for the construction of a simple host/vector complementing duo. This key enzyme in lactose metabolism hydrolyses lactose into glucose and galactose which are further metabolised. The amino acids residues of the N-terminal portion of the β-galactosidase are responsible of its tetramerization which represents the active quaternary conformation for this particular enzyme. Among the numerous mutants generated over the years the M 15 β-galactosidase is a truncated form presenting a deletion from residues 11 to 41. The M 15 mutant is an inactive dimer but can be complemented to the active tetrameric form by the addition of the lacZ α-peptide, containing the deleted residues, and present into numerous cloning vectors [11; 12]. This complementation has been used for years for cloning but, never to exert a selective pressure on the XLI *Escherichia coli* strain growth and force it to maintain a plasmid. To demonstrate this the XLI strain and XL1::pUCI9 were placed on minimal medium with lactose as carbon source. The XLI mutated strain alone lacking β-galactosidase activity was unable to grow due to it's incapacity to metabolise lactose, which was the only carbon source present on the plate. When trans complemented by the lacZ α peptide encoded by the commercially available PUC19 plasmid, or when plated on a minimal medium with another carbon source (such as glucose) it was possible to restore XL1 strain growth. This original and simple method allows plasmid bearing cells to be selected in a very straightforward way without addition of any further component to the culture medium. Since XL I-blue strain growth is limited only when lactose is the unique available carbon source, it is possible to prepare competent cells in the classical way using the standard LB medium. Again, transformants can be selected by plating them on minimal medium with lactose as the unique carbon source.

This autoselecting host/vector couple is a very attractive system for GMP production of recombinant proteins in microorganisms where synthetic mediums are routinely used.

As lactose assimilation may not be the most convenient carbon source for industrial applications, a different host/expression vector gene complementation duo has been developed in order to allows the use of any adequate carbon source. The *Escherichia coli* pyrC gene has then been consider for the development of a new host/vector complementation system. The gene and its promoter were PCR amplified from the bacterial chromosome and cloned into an expression vector. This gene is negatively regulated by pyrimidine availability in the bacteria cytoplasm by the formation of an hairpin at the 5' end of the pyrC transcript, which overlaps the pyrC ribosome binding site, and is required for repression of pyrC expression. Formation of the hairpin is dependant upon CTP and GTP intracellular concentration. Under conditions of pyrimidine limitation, pyrC transcripts are readily translated, resulting in a high level of dihydroorotase synthesis [13].

This tight gene regulation is an advantage from the energetic point of view and helps to keep the cell metabolic load as low as possible, preventing translation when unnecessary.

The pyrC gene was also selected since it is present on the *Escherichia coli* chromosome, as an isolated gene and not as part of an operon, in contrast to the majority part of the genes implicated in pyrimidine synthesis [14]. Another possible candidate was the pyrD gene but since the encoded protein location is in the membrane [15] its over-expression would have been deleterious for the purposes of the present invention. The data on plasmid stabilization with the pyrC gene complementation has shown that it is possible to obtain almost equivalent, and even better, results with the system of the present invention as compared to the classical antibiotic resistance system. This is in part due to the continuous selective pressure which is applied to the strain as soon as it grows in a minimal medium where it needs to synthesise it's pyrimidic bases. As the system acts on the DNA/RNA synthesis, the cell metabolism is blocked when the mutated *Escherichia coli* cell loses the expression vector. This system is quite different than the previously reported hok/sok stabilization procedure where both genes are encoded by the plasmid and which introduce, in plasmid free cells, the hok gene product corresponding to a potent cell-killing protein.

The pyrC system is a trans complementation of a natural *Escherichia coli* gene which has been deleted from the bacterial chromosome and cloned onto the plasmid and which when lost will introduce a strain auxotrophy and subsequent growth arrest. This system is different to the one described by Fiedler and Skerra [16] which is an auxotrophic complementation system based on the synthesis of the proline amino acid. This type of complementation is used by the authors as a second selection mechanism together with chloramphenicol resistance in order to abolish plasmid loss and to produce a JM83 *Escherichia coli* strain. The proAB genes were not deleted purposively from the strain as the strain was already carrying the mutation (as with many *Escherichia coli* strains) and those genes where cloned onto the expression vector to enable the strain to grow in a synthetic medium. It has not been demonstrated, however, that this system can be used alone to prevent plasmid loss during fermentation. This is probably due to the fact that proline-auxotrophy alone may not be selective enough during fermentation, as the microorganism may find some proline in the culture broth where proteins accumulate after a while. This type of regulation block protein synthesis whereas pyrC affects RNA or DNA synthesis which is an earlier event in the cell metabolism. But even in the presence of the chloramphenicol as the main selective agent the overall production does not exceed 20 mgL$^{-1}$ which is lower that the system of the present invention.

Degryse reported a complementation system based again on amino acid auxotrophy (lysine). The author has complemented an *Escherichia coli* strain deficient for diaminopimelate (DAP) which is the metabolic precursor of lysine and bacterial cell wall[17]. Again the complementation system was used in parallel with the cer gene which has been shown to reduce multimer formation and to increase plasmid stability [18]. The cer gene has a better stabilizing effect than the auxotrophy complementation itself. Although the author has stabilized the expression vector they do admit that, paradoxically, no increase can be detected in the recombinant protein expression level.

Other systems of gene complementation have been reported that need to be expressed from high copy number plasmids [19; 28]. These systems are difficult to use in a fermentation process where high copy number vectors induce a too high a metabolic stress to the bacterial strain which inevitably leads to cell lysis.

Thus in the first aspect the present invention provides a method of producing a recombinant protein comprising:—
(a) transforming a host cell lacking a gene encoding an enzyme required for nucleotide synthesis with a vector comprising a gene encoding the recombinant protein and the gene encoding the enzyme; and
(b) growing said host cell.

The host cell is preferably prokaryotic, more preferably a bacterium, most preferably *Escherichia coli*. In one preferred embodiment the enzyme is PyrC or a homologue thereof. The gene for the enzyme is preferably present in the wild type host cell as a single gene, as opposed to be part of an operon.

As used herein the term "homologue" relates to proteins which have a similar amino acid sequence, for instance proteins or polypeptides which include one or more additions, deletions, substitutions or the like are encompassed by the present invention. In addition, it may be possible to replace one amino acid with another of similar "type". For instance replacing one hydrophobic amino acid with another.

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

In the case of homologues and derivatives, the degree of identity with a protein or polypeptide as described herein is less important than that the homologue or derivative should retain the function of the original protein or polypeptide. However, suitably, homologues or derivatives having at least 60% similarity (as discussed above) with the proteins or polypeptides described herein are provided. Preferably, homologues or derivatives having at least 70% similarity, more preferably at least 80% similarity are provided. Most preferably, homologues or derivatives having at least 90% or even 95% similarity are provided.

The method is used preferably to produce human proteins, in particular antibodies or fragments thereof, preferably Fab fragments. Antibody fragments include, for example, Fab, $F(ab')_2$ and Fv fragments. Fv fragments can be modified to produce a synthetic construct known as a single chain Fv (scFv) molecule. This includes a peptide linker covalently joining $V_h$ and $V_l$ regions, which contributes to the stability of the molecule. Other synthetic constructs that can be used include CDR peptides. These are synthetic peptides comprising antigen-binding determinants. Peptide mimetics may also be used. These molecules are usually conformationally restricted organic rings that mimic the structure of a CDR loop and that include antigen-interactive side chains In a second aspect the present invention provides a host cell from which a gene encoding any enzyme required for nucleotide synthesis has been deleted. In one preferred embodiment the host cell is BW 25113[delta]pyrC. Hereinafter the word [delta] may be referred to as the Greek symbol "Δ".

In a third aspect the present invention provides a vector comprising a gene encoding an enzyme required for nucleotide synthesis. In one preferred embodiment the vector further comprises one or more promoters, or other regulatory elements. Suitable promoters are well known to those skilled in the art. As used herein the term "regulatory element" means other elements of a nucleic acid sequence that are involved in the regulation of gene expression such as polyadenylation sequences, enhancer elements, transcription terminators etc. Suitable sequences are well known to the person skilled in the art. The vector should also contain sequences required for replication of the vector, for example an origin of replication. The vector preferably contains a multiple cloning site.

In another aspect the present invention provides the use of a vector as defined herein in a method of expressing the recombinant protein.

In a fourth aspect the present invention provides a kit for expressing a recombinant protein comprising:
(a) a host cell as defined herein; and
(b) a vector as defined herein.

The present invention will now be described in detail by reference to the following examples. Preferred features of each aspect of the invention are as for each of the other aspects mutatis mutandis. The prior art documents mentioned herein are incorporated to the fullest extent permitted by law.

EXAMPLE 1

It was first demonstrated that it is possible to use gene complementation as a selective pressure to force a microorganism, e.g. *Escherichia coli*, to maintain the expression vector during cell growth. To this end the *Escherichia coli* XLI-blue strain [5] and pUC19 [6] expression vector, both commercially available, were identified as possible candidates to perform the gene complementation assay. The XLI-blue strain presents the mutation [delta](lacZ)MI5, which corresponds to the deletion of the "α-fragment" of the β-galactosidase enzyme. The α fragment is encoded by many cloning vectors such as pUC19 and can restore, by gene complementation, the β- galactosidase enzymatic activity to an *Escherichia coli* strain presenting the chromosomal deletion [delta](lacZ)MI5. A strain carrying this deletion will appear colourless when grown on X-gal plates, but when the α peptide complementation occurs, i.e. when the plasmid is present, the same strain will develop a blue phenotype. The pUC19 cloning vector on the one hand encodes for the β-lactamase gene and on the other hand possesses a multiple cloning sites positioned in the α-peptide. This multiple cloning sites was purposely inserted into this region to ease the screening of plasmids which have, after ligation, inserted a DNA fragment. DNA insertion in the α-peptide destroys its open reading frame, or folding, and abolishes β- galactosidase activity leading to colourless phenotype when grown on X-gal plates.

The β-galactosidase hydrolyses lactose into glucose and β-galactose and is one of the key enzymes in the lactose assimilation pathway. To test the hypothesis XLI-blue strain bacteria were transformed with pUC19 and cells were plated on LB agar/ampicillin.

Selected clones, all containing the expression vector, were then transferred on M9 minimal plates containing glucose or lactose as carbon source. In parallel the untransformed strain was tested for its growth on the same media (Table I).

TABLE I

Interdependence between β-galactosidase activity and cell growth
Growth on selective media

| Strain/plasmid | LB/Amp | M9/glucose | M9/Lactose |
|---|---|---|---|
| XL1-blue | − | + | − |
| XL1-blue/pUC 19 | + | + | + |

As shown in table I, only cells harbouring the expression vector are able to metabolise lactose and therefore to grow when it is the only available carbon source. This experiment shows that gene complementation between plasmid and host for a critical metabolic enzyme can be successfully used as selective pressure to force cells to maintain the expression vector. This simple system does not require any antibiotic addition to the medium to select plasmid bearing cells, and is only limited by the use of a defined medium with lactose as a carbon source.

EXAMPLE 2

Having demonstrated that the approach is correct, a more appropriate system was engineered for recombinant protein production. A key enzyme in *Escherichia coli* metabolism was identified as one whose absence prevents growth on minimal media but not on rich ones: the dihydroorotase enzyme[7] which is the product of the pyrC gene.

The dihydroorotase converts dihydroorotate into orotate which is then transformed in orotidylate which gives, after decarboxylation, the Uridylate or UMP, the essential pyrimidic nucleotide. After phosphorylation, UMP is converted in UTP which in turn provides CTP to the cell. Thus by deleting this enzyme it is possible to block RNA and DNA synthesis in their early steps. In complex mediums CTP and UTP are already present in the culture broth, so the dihydroorotase absence has no effect on microorganism growth in rich media whereas it prevents strain growth on minimal media.

The pyrC gene was entirely deleted from the chromosome[8] of *Escherichia coli* BW25113 strain to prevent possible homologous recombination with an expression vector bearing it. The new strain *Escherichia coli* BW25113ΔpyrC was deposited prior to the filing of the present application at the Collection Nationale de Cultures de Microorganismes (CNCM), Institut Pasteur, 25, Rue du Docteur Roux, Paris, in accordance with the Budapest Treaty and bears the following designation: CNCM I-3447.

In parallel, the entire pyrC gene with its own promoter were PCR amplified and cloned into pUC18 to generate pUCI8-pyrC. As a first approach, and in order to validate the complementation system, the pUC 18-pyrC was transformed into BW25113ΔpyrC strain and the resulting colonies were plated on several selective media (Table II).

TABLE II

Interdependence between pyrC presence and BW 25113 ΔpyrC strain growth on minimal medium.

| Medium (+kanamycin) | BW25113ΔpyrC | BW 25113ΔpyrC/ pUC18-pyrC + Amp | BW 25113ΔpyrC/ pUC18-pyrC − Amp |
|---|---|---|---|
| M9 + glucose | − | + | + |
| M9 + arabinose | − | − | − |
| LB | ++ | ++ | ++ |

The + or −signs reflect the ability of the microorganism to expand on those medium. The lack of growth on the arabinose carbon source is due to AaraBADAH33 mutation of the strain (see Material & Methods). The kanamycin resistance of the strain is due to the insertion of the kanamycin resistance gene on the *Escherichia coli* chromosome in the pyrC locus. The ++ sign relates a higher growth than the + one.

These results confirm i) that the strain BW 25113[delta] pyrC alone is not able to grow on minimal media if not complemented by the pyrC gene; ii) the functionality of the cloned pyrC gene and its correct deletion in the bacterial strain; iii) the incapacity of this strain to use arabinose as a carbon source which is an important parameter for gene expression from the arabinose promoter (see below).

EXAMPLE 3

In order to check plasmid stability dilutions of an over night culture, in minimal medium, were plated on LB agar and, the day after, some cfu were transferred onto M9/glucose minimal medium with or without ampicillin (Table III).

TABLE III

Plasmid stability after an overnight culture. After an overnight culture the cells were diluted to the appropriate density and plated on LB agar. Forty cfu were then transferred on selective medium to determine plasmid presence.

| Medium | % of plasmid possessing cells |
|---|---|
| M9 + glucose + Amp | 100 |
| M9 + glucose | 100 |

This experiment demonstrates that the plasmid was present in all the tested cells even after an overnight culture since cfu present on the LB plate are still able to grow on minimal medium.

Next it was determined if the investigated pyrC based stabilization system would still be efficient, even in the presence of a high metabolic charge of the microorganism such as during the production of a recombinant protein, which normally stimulates the strain to throw out the expression vector. To do so, DoB 0114 (FIG. 1) a pBAD derivative expression vector (Invitrogene™), in which the bla gene was substituted with for one tetracycline resistance, was used as reference plasmid. This home designed bi-cistronic expression vector was engineered to express the C4[9] human Fab fragment into the *Escherichia coli* periplasmic space. Since the Fab fragment is a small and soluble protein, it diffuses from the *E. coli* periplasmic space to the culture supernatant where it is collected and easily purified.

DoB 0138 (FIG. 2) was derived from DoB 0114 by substituting the antibiotic resistance gene with pyrC. The expression vectors DoB 0114 and DoB 0138 were respectively transformed into a W3110 ara strain[10] and BW 25113[delta] pyrC strain. After transformation, in order to select one cfu bearing the expression vector to inoculate the culture, W3110::DoB 0114 was plated on LB agar/Tetracyclin, whereas BW 25113[delta]pyrC::DoB 0138 was plated on M9 minimal medium with glucose as carbon source. A single cfu was used to inoculate a 10 ml shaking flask culture in minimal medium supplemented with a sugar as carbon source (and tetracycline for DoB 0114). After 15 hours at 30° C. the 10 ml were used to inseminate 90 ml, of the same broth, and incubated for 13 hours at 37° C. The 100 ml shaking flask culture was used to inoculate a 1 liter fermenter. When the $OD_{600}$ reached 10-12 the percentage of plasmid bearing cells was determined, and recombinant protein production was turned on by addition of 5 grams of arabinose ($T_0$). After 16 hours of induction when $OD_{600}$ reaches 30 ($T_{16}$) the fermentation was stopped and the quantity of recombinant Fab fragments and proteins in the culture supernatant were determined (Table IV).

TABLE IV determination of the percentage of transformed cells and related recombinant protein yield

| DoB | Selection | % transformed cells ($T_o$) | Protein concentration at $T_{16}$ (mg/L) | |
|---|---|---|---|---|
| | | | Fab | Total |
| 0114 | Tetracyclin* | 96 | 1.8 | 464 ± 133 |
| 0138 | PyrC | 98 | 6.6 | 614 ± 95 |

Fab concentration was determined by RP-HPLC whereas total protein concentration was assessed by Bradford analysis.
*Tetracyclin was added only in the inoculum culture and not during fermentation.

The results of this experiment demonstrates that even if, at the moment of induction, the number of transformed cells are equivalent for both vectors, at the end of the culture the overall production yield of DoB 0138 is surprisingly more than three time that of DoB 0114, whereas the total protein concentration present in the culture supernatant remain almost unchanged. These results may be explained by a higher plasmid stability for DoB 0138 than for DoB 0114 during the induction culture phase. The percentage of transformed cells was determined as previously described: cells were first plated on LB agar and then transferred on selective media (LB agar+tet for DoB 0114 or M9 glucose for DoB 0138). If this methods does work perfectly before induction, the high metabolic charge of the induced microorganism slows its growth in such a dramatic manner that it become almost impossible to observe any colony formation on plates. This hypothesis was confirmed by plating a non-induced cfu, from an LB plate, onto an M9 and M9/arabinose plate. Any growth observed on the M9 minimum is unable to expand on M9/arabinose. This extreme slow growth, ascribable to elevated metabolic charges of the induced microorganism, forbids the isolation of individual cells in order to determine the percentage of vector maintenance during the induction phase.

EXAMPLE 4

Having demonstrated that the stabilization system, by gene complementation, gave better results than the classic system, a fermentation was performed on the ten liters scale including this time a fed batch system to investigate the method scalability. Substrate concentration was raised to 60 g/l and the fermenter (starting with 7.2 liters) was inoculated with 800 ml of pre-culture. After a batch period of approximately 17 hours feeding was started with a sugar solution as a carbon source and arabinose as inducer. The fed-batch control was set on the dissolved oxygen (DO) value which turned on the feeding pump when the 50% value was exceeded. After 20 hours of fed batch the culture $OD_{600}$ reached 150-160 and the supernatant containing the Fab harvested (Table V).

TABLE V determination of the percentage of plasmid bearing cells and related recombinant protein yield after fed-batch fermentation.

| DoB | Selection | % transformed cells ($T_o$) | Protein concentration at $T_{20}$ (mg/L) | |
|---|---|---|---|---|
| | | | Fab | Total |
| 0114 | Tet | 100 | 40.2 | 1884 ± 180 |
| 0138 | PyrC | 100 | 84.6 | 1202 ± 130 |

These results demonstrate the scalability of the method and that even after a higher number of generations the expression vector stability was still fulfilling expectations. This time, due to the fed batch system the overall Fab yield was ten times superior to the one liter batch culture but the PyrC complementation system is still producing twice the amount of the DoB 0114 "classical" vector.

EXAMPLE 5

In order to demonstrate that the observed differences in the Fab production yield were not strain dependant (ie W3110 vs BW25113) we an ultimate experiment was planed where the two expression vectors were transformed in BW25113. The fermentation protocol was slightly modified and the induction phase was further extended for 6 extra hours.

Figure 3:
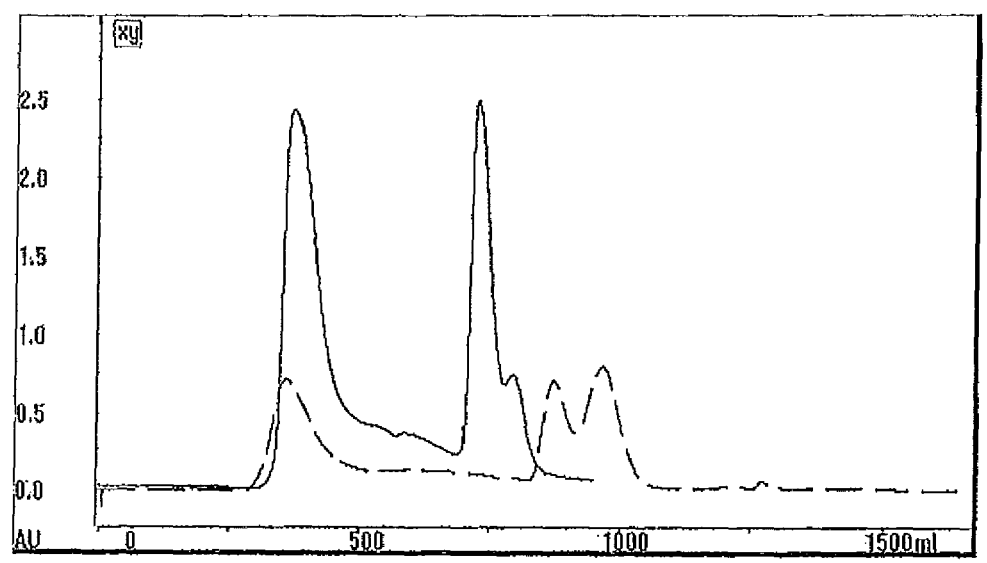
FIG. 3 SP-Sepharose Fast flow column (Amersham Bioscience) elution of two fermentation supernatants corresponding to the PyrC stabilized system (DoB) 0138-plain line) and the TET stabilized expression vector (DoB 0114-dashed line).

At the end of the fermentation supernatant was acidified to pH6 and pass through a SP-Sepharose Fast flow column (Amersham Biosciences). Due to the Fab elevated isoelectric point, in those conditions and at this pH, the Fab is almost the only protein to be retain by the resin and elute in the first peak where it represent more than 80% of the proteins. After adsorption and washing the resin was eluted and the fraction corresponding to the Fab harvested. The result of the experiment is reported in the FIG. 3. The overall Fab production was estimated to be around 100 mg per liter for the PyrC system (DoB 0138-plain line) and yield of less than 50% was obtained for the TET stabilized expression vector (DoB 0114-dashed line).

During fermentation we observed a faster growth for DoB 0114 which terminate the two liters of feeding solution after 22 hours of induction whereas at the same time DoB 0138 only consumed 1.35 liters. This fast growing rate do correctly correlate with the lower metabolic yield of the microorganism, the relatively low production of recombinant protein and to the high production of host cell proteins. In fact with DoB 0114 the Fab represent much lower percentage of the proteins present in supernatant as compare to the DoB 0138. In the second case having a higher overall recombinant protein yield provides material easier to purify since the recombinant protein which can be estimated to 10% of the soluble protein is already 10% "pure".

Figure 4:
FIG. 4 PCR detection of expression vector.

Since the only difference between the two system is the selective pressure which is continuous in the case of the pyrC we have set up a PCR protocol in order to check for expression vector presence during fermentation. A pair of primers corresponding to the carboxy terminus part of the Fab heavy chain was used to PCR amplify the expression vector directly from culture broth opportunely normalized to 0.1 $OD_{600nm}$ to compensate cell (and therefore template) multiplication. As shown in FIG. 4 the signal corresponding to DoB 0138 is stable during fermentation time whereas for DoB 0114 it decrease to a faint imperceptible band after 26 hours of induction.

Material & Methods

Medium

Mineral salts medium components together with water were autoclaved at 121° C. for 20 min in situ. Initial sugar was sterilised separately by filtration 0.22 µm and added to the bioreactor giving a concentration of 40.0 g/l to create a small batch phase before the feed phase was started. Ten milliliters trace elements solution, and vitamins were added by sterile filtration to the already sterile bioreactor. Composition of the trace elements solution was (g per liter): $C_6H_5Na_3O_7*2H_2O$, 100.0; I $CaCl_2*2H_2O$, 3.40; $ZnSO_4*7H_2O$, 2.40; $MnSO_4*2H_2O$, 1.50; $CuSO_4*5H_2O$, 0.50; $CoCl_2*6H_2O$; $FeCl_3*6H_2O$, 9.70; $H_3BO_3$, 0.03; $Na_2MoO_4*2H_2O$, 0.02; KCl, 74.5. The feed contained 70% sugar solution. Composition of the feed induction solution was: sugar 70%; vitamins and arabinose. Antifoam 204 was added when needed for foam control.

Cultivation

A primary seed culture was prepared by growing cells in 100 ml shaking flask containing 25 ml of bioreactor medium except for sugar concentration 5.0 g/l. This culture was grown at 37° C. and 245 rpm for 15 h. Sixteen ml of primary seed culture was used as inoculum for two 2 liters baffled flask contained 400 ml of the same medium and grown in the same conditions. The secondary seed culture was transferred to a CF 3000 (Chemap) 15-1 bioreactor with a working volume of 10 L. The fermenter was equipped with an air sparger and airflow was initially set to 8 l/min and stepwise elevated to 10 l/min after feed start. The stirrer speed was increased from 800 to 1200 rpm during the batch period and decreased to 1000 rpm during the fed-batch part. A polarographic oxygen electrode was used to register the dissolved oxygen (DO). The fermenter was equipped with pH titration to keep a pH of 6.95 by addition of 30% (w/w) ammonia solution. Temperature was controlled at 37° C. Feeding was started when the DO increased after exhaustion of the initially added sugar. During the first fed-batch phase 230 ml of sugar feeding solution was added by using a DO-STAT control with the oxygen concentration set point fixed at 50% saturation. The protein expression phase was started by shifting to the feeding solution containing arabinose as the inducer, maintaining the same DO-STAT strategy for 30 h.

Sampling

Sampling was performed every hour throughout all cultivations.

Analyses

Protein concentration measurement: Protein concentration was determined by Bio-Rad protein assay. The assay was carried out in a 96/well microplate. Increasing amounts (from 0.25 to 8 µg per well) of BSA were included to create a reference protein concentration standard curve. In each well 50 µl of dye solution was mixed with 150 µl of sample, then the $A_{595}$ was read in a Model 450 Microplate Reader (Bio-Rad).

Recombinant Protein Expression (Gel Electrophoresis and Western Blot)

Samples were subjected to non reducing 15% SDS-PAGE according to Laemmeli (21), with minor modification, in a Mini-Protean II apparatus (Bio-Rad). In some experiments, gels were run under reducing conditions. Broad molecular weight standards (Bio-Rad) were used to determine the apparent molecular weight of electrophoretic bands. Mini-gels of 1.0 mm thickness were run at 50 I mA for 1 h, stained overnight in a 0.02% Phast Gel Blue R (Pharmacia) solution made in 40% $CH_3OH$, 10% $CH_3COOH$, and de-stained in 20% $CH_3OH$, 5% $CH_3COOH$.

Western blot analysis were performed according to Towbin et al. (22), with minor modification. Samples run of 15% of SDS-PAGE were transferred to a 0.45 µm nitrocellulose membrane at 1 $mA/cm^2$ for 90 min in a multiphor II semidry apparatus (Pharmacia). Membranes were stained with a Ponceau-S solution (Sigma, U.S.A.), The relevant molecular weight standards were marked, and complete destaining was achieved by rinsing in 20 mM Tris-HCl, pH 7.40, 150 mM NaCl (TBS). Membranes were saturated overnight with a 2% BSA solution in TBS (BT), then incubated for 1 h with a 1:2000 dilution of Peroxidase-Conjugated Rabbit Anti-Human lambda Light Chains (DAKO) in BT containing 0.05% Tween 20 (BTT). Afterwards the membrane was washed with once for 10 min in BTT, once with 0.25% Tween 20 in TBS, and several times in TBS. All incubations were performed in a shaking platform at room temperature. The peroxidase activity was revealed by SuperSignal West Fico Chemiluminescent Substrate (PIERCE).

HPLC analysis

Quantification of soluble Fab in the fermentation broth was carried out, after a clarification step done by centrifugation at 17000×g for 15 minutes by HPLC equipped with an Diphenyl 219TP54, 250×4.6 mmID, 300 Å column VYDAC and a florescence detector (ex λ:285 nm; em λ=360 nm; gain 1000). In addition the same supernatant aliquots were analysed for sugar, acetate and arabinose by HPLC equipped with an PL Hi-Plex H 8 µm, 300×7.7 mm, 8 µm or equivalent column and a refractive index detector.

Molecular Biology

Construction of the *Escherichia coli* BW25113, ΔpyrC strain.

The pyrC mutant was realized as according to Datsenko and Wanner which allows defined deletions in the *Escherichia coli* chromosome. The selected was BW25113 (lacI$^q$, rrnB$_{T14}$, Δ lacZ$_{WJ16}$, hsdR514, ΔaraBA-D$_{AH33}$, Δrha-BAD$_{LD78}$). The whole gene with its own promoter was removed to avoid homologous recombination with the plasmid copy. The primers used to delete the gene where:

```
dispyrC-f:
SEQ ID NO: 1:   5'-AATTGTCATT CCATTTACTG ATTAATCACG
                AGGGCGCATT GTGTAGGCTG GAGCTGCTTC-3'
and dispyrC-r:
SEQ ID NO: 2:   5'- ACAGGTAAAA TAACCTAATG ACAACAGGAA
                GCTACGATTT ATTCCGGGGA TCCGTCGACC-3'.
```

The kanamycin resistance gene was not remove form the strain chromosome to serve as potential positive selection for the strain itself.

PUC18-pyrC:

The pyrC gene was PCR retrieved from the *Escherichia coli* chromosome using the following primers:

```
pyrC-fwd:
SEQ ID NO: 3:
5'-ATATACCATG GCGCGCCCTT TATTTTTCGT GC-
3';

pyrC-rev:
SEQ ID NO: 4:
5'- GTT AACCA TG GTT A TTGTTT AACGGACCAG
CGT AC-3'
``` and cloned into the SmaI site of pUC18 and the resulting vector was called pUC-pyrC.

Construction of DoB 0114:

The vector DoB 0114 was obtained from the pBAD/Myc-His A, B, C vector (Invitrogen) by substitution of the ampicillin gene by the tetracycline one of PBR322. The C4 expression cassette was assembled with the following oligonucleotides and pHEN1 expression vector [9] as template:

```
"PI C4"
SEQ ID NO: 5:
5'- AAA AAA AAC ATC GCA TTC CTG CTG GCA TCT

ATG TTC GTT TTC TCT ATC GCA ACC AAC GCA TAC GCA

CAG TCT GCC CTG ACT CAG CCT-3';

"P2 C4"
SEQ ID NO: 6:
5'- GGT TAA TTT CTC CTT CTA TGA ACA TTC TGT

AGG GG-3';

"P3 C4"
SEQ ID NO: 7:
5'- TCA TAG AAG GAG AAA TTA ACC ATG AAA AAA

AAC ATC GCT TTC CTG CTG GCT TCC ATG TTC GTT TTC

TCC A TC GCT ACC AAC GCT T AC GCT CAG GTG CAG CTG

GTG GAG TCT-3;

"P4 C4"
SEQ ID NO: 8:
5'- TCA GGA GGT TTT GTC GCA GGA TTT GGG CTC

AAC T-3';

"P5 C4"
SEQ ID NO: 9:
5'- AAA AAA AAC ATC GCA TTC CTG CTG GCA -3',

"P6 C4"
SEQ ID NO: 10:
5'- CCC GCT CGA GTC AGG AGG TTT TGT CGC AGG

A-3'.
```

Figure 5:
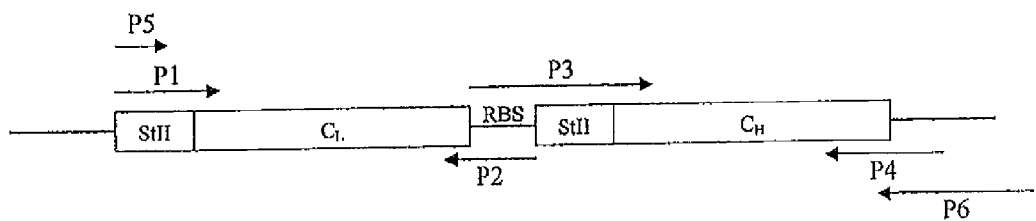
FIG. 5 Cassette assembly scheme to PCR amplify and clone an Fab fragment.

Primers PI and P2 were used in a first PCR to amplify the Fab light chain and add in frame the StII leader sequence. A second PCR was run to separately amplify the Fab heavy chain and add the StII leader sequence and the intergenic sequence. Since the two sequences are overlapping (see cartoon) PCR products resulting from the first two amplifications were mixed together in a third elongation reaction, for ten cycles, where no primers were added. After the elongation step primers P5 and P6 were added to the PCR and the full length expression cassette was amplified as reported in FIG. 5.

The final PCR product was digested with the XhoI restriction enzyme and cloned into the pBAD vector opened with NcoI (klenow) XhoI. Cfu were screened by PCR and a positive clone sequenced for the entire Fab expression cassette. A clone presenting the expected sequence was named DoB 0114 (FIG. 1).

Figure 2:
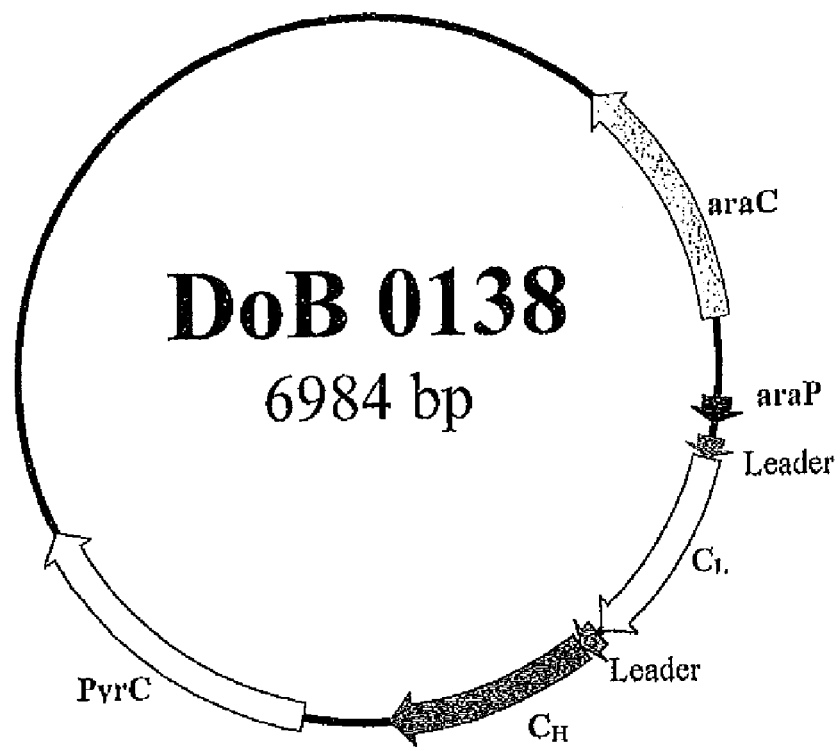
FIG. 2 Map of DoB 0138 expression vector based on PyrC complementation stabilization.

Construction of DoB 0138:

This expression vector was obtained by the substitution of the HindIII-NruI DNA fragment of DoB 0114, coding for tetracycline resistance, with the pyrC gene obtained by EcoRI/kIenow-HindIII digestion of pUC-pyrC plasmid (FIG. 2).

PCR detection of expression vector

To detect/amplify the expression vector a PCR was run on a sample of culture broth diluted to 0.1 OD600 nm in order to normalize cell number. PCR cycles were set as reported in the next table.

| Step | Temperature | Time | Cycles |
|------|-------------|---------|--------|
| 1 | 94° C. | 4 min. | 1 |
| 2 | 94° C. | 1 min. | 30 |
| 3 | 60° C. | 1 min. | |
| 4 | 72° C. | 1 min. | |
| 5 | 72° C. | 10 min. | 1 |

```
Primers:
247 CH sense PCN 5'
SEQ ID NO: 11:    GGAGTGGGTCTCATCCATT -3' Tm = 61.4

248 CH AS PCN5'
SEQ ID NO: 12:    GACCTTGGTGTTGCTGGG -3' Tm = 64.3
```

The PCR product is about 500 by for Fab heavy chain.

The expression system of the present invention allows rapid selection of plasmid containing cells during the cloning phases and lead to high protein expression during fermentation. This system has a strong selective efficiency, especially during the induction phase, leading to the selection of an almost homogeneous plasmid bearing cell population. Moreover the productivity of the culture is to a large extent better than the one based on antibiotic resistance. This elevated vector stability combined with its high productivity fulfils the requirements for heterologous protein production in *Escherichia coli* to an industrial level. It has been further demonstrated that the engineered strain was a better strain for Fab production than the classical W3110 and that it's ΔpyrC derivative was suitable for high cell density fed batch fermentation and therefore open to industrial exploitation.

```
SEQ ID NO: 13: Sequence of PyrC gene as inserted in pUC18
cloning vector
    1 ATATACCATG GCGCGCCCTT TATTTTTCGT GCAAAGGAAA ACGTTTCCGC
      TATATGGTAC CGCGCGGGAA ATAAAAAGCA CGTTTCCTTT TGCAAAGGCG 51 TTATCCTTTG TGTCCGGCAA AAACATCCCT TCAGCCGGAG CATAGAGATT
      AATAGGAAAC ACAGGCCGTT TTTGTAGGGA AGTCGGCCTC GTATCTCTAA M  T  A   P  S  Q   V  L  K   I  R  R   P  D  D  W  H  .
  101 AATGACTGCA CCATCCCAGG TATTAAAGAT CCGCCGCCCA GACGACTGGC
      TTACTGACGT GGTAGGGTCC ATAATTTCTA GGCGGCGGGT CTGCTGACCG .  L  H  L   R  D  G   D  M  L  K   T  V  V   P  Y  T
  151 ACCTTCACCT CCGCGATGGC GACATGTTAA AAACTGTCGT GCCATATACC
      TGGAAGTGGA GGCGCTACCG CTGTACAATT TTTGACAGCA CGGTATATGG
```

```
              S   E   I   Y      G   R   A      I   V   M      P   N   L   A      P   P   V .
201 AGCGAAATTT ATGGACGAGGC TATCGTAATG CCCAATCTGG CTCCGCCCGT
    TCGCTTTAAA TACCTGCCCG ATAGCATTAC GGGTTAGACC GAGGCGGGCA

. T   T   V      E   A   A   V      A   Y   R      Q   R   I      L   D   A   V .
251 GACCACCGTT GAGGCTGCCG TGGCGTATCG CCAGCGTATT CTTGACGCCG
    CTGGTGGCAA CTCCGACGGC ACCGCATAGC GGTCGCATAA GAACTGCGGC

. P   A   G      H   D   F      T   P   L   M      T   C   Y      L   T   D
301 TACCTGCCGG GCACGATTTC ACCCCATTGA TGACCTGTTA TTTAACAGAT
    ATGGACGGCC CGTGCTAAAG TGGGGTAACT ACTGGACAAT AAATTGTCTA

S   L   D   P      N   E   L      E   R   G      F   N   E   G   V      F   T .
351 TCGCTGGATC CTAATGAGCT GGAGCGCGGA TTTAACGAAG GCGTGTTCAC
    AGCGACCTAG GATTACTCGA CCTCGCGCCT AAATTGCTTC CGCACAAGTG

. A   A   K      L   Y   P   A      N   A   T      T   N   S      S   H   G   V .
401 CGCTGCAAAA CTTTACCCGG CAAACGCAAC CACTAACTCC AGCCACGGCG
    GCGACGTTTT GAAATGGGCC GTTTGCGTTG GTGATTGAGG TCGGTGCCGC

. T   S   I      D   A   I      M   P   V   L      E   R   M      E   K   I
451 TGACGTCAAT TGACGCAATC ATGCCGGTAC TTGAGCGCAT GGAAAAAATC
    ACTGCAGTTA ACTGCGTTAG TACGGCCATG AACTCGCGTA CCTTTTTTAG

G   M   P   L      L   A   H      G   E   V      T   H   A   D      I   D   I .
501 GGTATGCCGC TACTGGCGCA TGGTGAAGTG ACACATGCAG ATATCGACAT
    CCATACGGCG ATGACCGCGT ACCACTTCAC TGTGTACGTC TATAGCTGTA

. F   D   R      E   A   R   F      I   E   S      V   M   E      P   L   R   Q .
551 TTTTGATCGT GAAGCGCGCT TTATAGAAAG CGTGATGGAA CCTCTGCGCC
    AAAACTAGCA CTTCGCGCGA AATATCTTTC GCACTACCTT GGAGACGCGG

. R   L   T      A   L   K      V   V   F   E   H      I   T      T   K   D
601 AGCGCCTGAC TGCGCTGAAA GTCGTTTTTG AGCACATCAC CACCAAAGAT
    TCGCGGACTG ACGCGACTTT CAGCAAAAAC TCGTGTAGTG GTGGTTTCTA

A   A   D   Y      V   R   D      G   N   E      R   L   A   A      T   I   T .
651 GCTGCCGACT ATGTCCGTGA CGGAAATGAA CGGCTGGCTG CCACCATCAC
    CGACGGCTGA TACAGGCACT GCCTTTACTT GCCGACCGAC GGTGGTAGTG

. P   Q   H      L   M   F   N      R   N   H      M   L   V      G   G   V   R .
701 TCCGCAGCAT CTGATGTTTA ACCGCAACCA TATGCTGGTT GGAGGCGTGC
    AGGCGTCGTA GACTACAAAT TGGCGTTGGT ATACGACCAA CCTCCGCACG

. P   H   L      Y   C   L      P   I   L   K      R   N   I      H   Q   Q
751 GTCCGCACCT GTATTGTCTA CCCATCCTCA AACGTAATAT TCACCAACAG
    CAGGCGTGGA CATAACAGAT GGGTAGGAGT TTGCATTATA AGTGGTTGTC

A   L   R   E      L   V   A      S   G   F      N   R   V   F      L   G   T .
801 GCATTGCGTG AACTGGTCGC CAGCGGTTTT AATCGAGTAT TCCTCGGTAC
    CGTAACGCAC TTGACCAGCG GTCGCCAAAA TTAGCTCATA AGGAGCCATG

. D   S   A      P   H   A   R      H   R   K      E   S   S      C   G   C   A .
851 GGATTCTGCG CCACATGCAC GTCATCGCAA AGAGAGCAGT GCGGCTGCG
    CCTAAGACGC GGTGTACGTG CAGTAGCGTT TCTCTCGTCA ACGCCGACGC

. G   C   F      N   A   P      T   A   L   G      S   Y   A      T   V   F
901 CGGGCTGCTT CAACGCCCCA ACCGCGCTGG GCAGTTACGC TACCGTCTTT
    GCCCGACGAA GTTGCGGGGT TGGCGCGACC CGTCAATGCG ATGGCAGAAA

E   E   M   N      A   L   Q      H   F   E      A   F   C   S      V   N   G .
951 GAAGAAATGA ATGCTTTGCA GCACTTTGAA GCATTCTGTT CTGTAAACGG
    CTTCTTTACT TACGAAACGT CGTGAAACTT CGTAAGACAA GACATTTGCC

. P   Q   F      Y   G   L   P      V   N   D      T   F   I      E   L   V   R .
1001 CCCGCAGTTC TATGGGTTGC CGGTCAACGA CACATTCATC GAACTGGTAC
     GGGCGTCAAG ATACCCAACG GCCAGTTGCT GTGTAAGTAG CTTGACCATG

. E   E   Q      Q   V   A      E   S   I   A      L   T   D      D   T   L
1051 GTGAAGAGCA ACAGGTTGCT GAAAGCATCG CACTGACTGA TGACACGCTG
     CACTTCTCGT TGTCCAACGA CTTTCGTAGC GTGACTGACT ACTGTGCGAC

V   P   F   L      A   G   E      T   V   R      W   S   V   K      Q
1101 GTGCCATTCC TCGCCGGGGA AACGGTACGC TGGTCCGTTA AACAATAACC
     CACGGTAAGG AGCGGCCCCT TTGCCATGCG ACCAGGCAAT TTGTTATTGG

1151 ATGGTTAAC
     TACCAATTG
```

REFERENCES

1. B. Hoffman; J. A. Broadwater,; P. Johnson; J. Harper; B. G. Fox and W. R. Kenealy. Proto Exp. Punf. 6, 646-654 (1995). Lactose fed-btach overexpression of recombinant metalloproteins in *Escherichia coli* BL21(DE3): process control yielding high levels of metal-incorporated, soluble protein.
2. Murphy, D. B. and Epstein, S. L. (1998) Guidance for Industry. Guidance for Human Somatic Cell Therapy and Gene Therapy. Food and Drug Administration, Rockville, Md.
3. Gerdes K, Helin K, Christensen O W, Lobner-Olesen A. *J Mol Bioi* 1988 september 5; 203(1):119-29. Translational control and differential RNA decay are key elements regulating postsegregational expression of the killer protein encoded by the parB locus of plasmid RI.
4. Pecota D C, Osapay G, Selsted M E, Wood T K. J Biotechnol 2003 January 9; 100(1):1-12. Antimicrobial properties of the *Escherichia coli* RI plasmid host killing peptide.
5. Bullock, W. O., J. M. Fernandez, and J. M. Short. 1987. XII-Blue, a high efficiency plasmid transforming recA *Escherichia coli* strain with beta galactosidase selection. Focus 5:376-378.
6. Yanisch-Perron C.; Vieira J and Messing J. Gene. 1985; 33(1):103-19. Improved M13 phage cloning vectors and host strains: nucleotide sequences of the M13 mp 18 and pUC19 vectors.
7. Backstrom D, Sjoberg R M, Lundberg L G. Eur J Biochem 1986 October 1; 160(1):77-82 Nucleotide sequence of the structural gene for dihydroorotase of *Escherichia coli* K12.
8. Datsenko K A, Wanner B L. Proc Natl Acad Sci USA. 2000 June 6; 97(12):6640-5. One-step inactivation of chromosomal genes in *Escherichia coli* K-12 using PCR products.
9. Figini M, Obici L, Mezzanzanica D, Griffiths A, Colnaghi M I, Winter G, Canevari S. Cancer Res. 1998 March 1; 58(5):991-6. Panning phage antibody libraries on cells: isolation of human Fab fragments against ovarian carcinoma using guided selection.
10. Duenas M, et al. Biotechniques 1994 March; 16(3):476-7, 480-3. Intra- and extracellular expression of an scFv antibody fragment in *E. coli*: effect of bacterial strains and pathway engineering using GroES/L chaperonins.
11. Gallagher C N, Huber R E. J Protein Chem 1998 February; 17(2):131-41 Studies of the M15 beta-galactosidase complementation process.
12. Langley K E, Zabin I. Biochemistry 1976 November 2; 15(22):4866-75: beta-Galactosidase alpha complementation: properties of the complemented enzyme and mechanism of the complementation reaction.
13. Wilson H R, Archer C D, Liu J K, Turnbough C L Jr. J Bacteriol 1992 January; 174(2):514-24; Translational control of pyrC expression mediated by nucleotide-sensitive selection of transcriptional start sites in *Escherichia coli*.
14. Sato T, Ohki M, Yura T, Ito K. J Bacteriol 1979 May; 138(2):305-13; Genetic studies of an *Escherichia coli* K-12 temperature-sensitive mutant defective in membrane protein synthesis.
15. Larsen I N, Jensen K F. Eur J Biochem 1985 August 15; 151(1):59-65; Nucleotide sequence of the pyrD gene of *Escherichia coli* and characterization of the flavoprotein dihydroorotate dehydrogenase.
16. Fiedler M, Skerra A. Gene. 2001 Aug. 22; 274(1-2): 111-8; proBA complementation of an auxotrophic *E. coli* strain improves plasmid stability and expression yield during fermenter production of a recombinant antibody fragment.
17. Degryse E. J Biotechnol. 1991 April; 18(1-2):29-39. "Stability of a host-vector system based on complementation of an essential gene in *Escherichia coli*."
18. Summers D K, Sherratt D J. Cell. 1984 April; 36(4):1097-103. Multimerization of high copy number plasmids causes instability: ColE 1 encodes a determinant essential for plasmid monomerization and stability.
19. Porter R D, Black S. J. Bacteriol. 1991 April; 173(8):2720-3. The single-stranded-DNA-binding protein encoded by the *Escherichia coli* F factor can complement a deletion of the chromosomal ssb gene.
20. Rocky M. Cranenburgh, Julian A. J. Hanak, Steven G. Williams and David J. Sherratt; Nucleic Acids Research, 2001, Vol. 29, No. 5 e26; 2001 *Escherichia coli* strains that allow antibiotic-free plasmid selection and maintenance by repressor titration.
21. Laemmli, U.K. (1970) Cleavage of structural proteins during the assembly of the head of bacteriophage T4. *Nature* 277,680-685.
22. Towbin, R., Staehelin, T. and Gordon, J. (1979) Electrophoretic transfer of proteins from polyacrylamide gels to nitrocellulose sheets. *Proc. Natl. Acad. Sci. USA* 76, 4350-4354.

The invention claimed is:

1. A method of producing a recombinant protein comprising:
   (a) transforming *Escherichia coli* strain BW25113ΔpyrC, having Collection Nationale de Cultures de Microorganismes designation number CNCM I-3447 with a vector comprising a gene encoding the recombinant protein and a wild-type *E. coli* pyrC gene; and
   (b) growing the transformed *Escherichia coli* of step (a) under conditions of pyrimidine limitation to thereby produce the recombinant protein.

2. The method as claimed in claim 1 wherein said recombinant protein is a human protein.

3. The method as claimed in claim 1 wherein said recombinant protein is an antibody or a fragment thereof.

4. The method as claimed in claim 3 wherein said antibody fragment is a Fab fragment.

5. *Escherichia coli* strain BW25113ΔpyrC, having Collection Nationale de Cultures de Microorganismes designation number CNCM I -3447.

6. A vector comprising vector pUC18 and a polynucleotide comprising the nucleotide sequence of SEQ ID NO:13, wherein vector pUC18 has a SmaI restriction enzyme site and the polynucleotide is inserted into the SmaI restriction enzyme site.

7. The vector as claimed in claim 6 further comprising a gene encoding a desired recombinant protein.

8. The vector as claimed in claim 7 wherein said desired recombinant protein is an antibody or a fragment thereof.

9. A kit for expressing a recombinant protein comprising:
   (a) *Escherichia coli* strain BW25113ΔpyrC, having Collection Nationale de Cultures de Microorganismes designation number CNCM I-3447; and
   (b) a vector comprising a gene encoding a wild-type *E. coli* pyrC gene.

10. *Escherichia coli* strain BW25113ΔpyrC, having Collection Nationale de Cultures de Microorganismes designation number CNCM I-3447 transformed with a vector comprising a gene encoding a desired recombinant protein and a wild-type *E. coli* pyrC gene.

11. A kit for expressing a recombinant protein comprising:
    (a) *Escherichia coli* strain BW25113ΔpyrC, having Collection Nationale de Cultures de Microorganismes designation number CNCM I-3447; and
    (b) a vector comprising vector pUC18 and a polynucleotide comprising the nucleotide sequence of SEQ ID NO:13, wherein vector pUC18 has a SmaI restriction enzyme site and the polynucleotide is inserted into the SmaI restriction enzyme site of pUC18.

12. The method of claim 1, wherein the vector further comprises vector pUC18 and a polynucleotide comprising the nucleotide sequence of SEQ ID NO:13, wherein vector pUC18 has a SmaI restriction enzyme site and the polynucleotide is inserted into the SmaI restriction enzyme site of pUC18.

* * * * *

SEQUENCE LISTING

<160> NUMBER OF SEQ ID NOS: 13

<210> SEQ ID NO 1
<211> LENGTH: 60
<212> TYPE: DNA
<213> ORGANISM: Escherichia coli

<400> SEQUENCE: 1
aattgtcatt ccatttactg attaatcacg agggcgcatt gtgtaggctg gagctgcttc        60

<210> SEQ ID NO 2
<211> LENGTH: 60
<212> TYPE: DNA
<213> ORGANISM: Escherichia coli

<400> SEQUENCE: 2
acaggtaaaa taacctaatg acaacaggaa gctacgattt attccgggga tccgtcgacc        60

```
<210> SEQ ID NO 3
<211> LENGTH: 32
<212> TYPE: DNA
<213> ORGANISM: Escherichia coli

<400> SEQUENCE: 3
atataccatg gcgcgccctt tattttcgt gc                              32

<210> SEQ ID NO 4
<211> LENGTH: 35
<212> TYPE: DNA
<213> ORGANISM: Escherichia coli

<400> SEQUENCE: 4
gttaaccatg gttattgttt aacggaccag cgtac                          35

<210> SEQ ID NO 5
<211> LENGTH: 87
<212> TYPE: DNA
<213> ORGANISM: Human

<400> SEQUENCE: 5
aaaaaaaaca tcgcattcct gctggcatct atgttcgttt tctctatcgc aaccaacgca   60
tacgcacagt ctgccctgac tcagcct                                   87

<210> SEQ ID NO 6
<211> LENGTH: 35
<212> TYPE: DNA
<213> ORGANISM: Human

<400> SEQUENCE: 6
ggttaatttc tccttctatg aacattctgt agggg                          35

<210> SEQ ID NO 7
<211> LENGTH: 111
<212> TYPE: DNA
<213> ORGANISM: Human

<400> SEQUENCE: 7
tcatagaagg agaaattaac catgaaaaaa acatcgctt tcctgctggc ttccatgttc    60
gttttctcca tcgctaccaa cgcttacgct caggtgcagc tggtggagtc t         111

<210> SEQ ID NO 8
<211> LENGTH: 34
<212> TYPE: DNA
<213> ORGANISM: Human

<400> SEQUENCE: 8
tcaggaggtt ttgtcgcagg atttgggctc aact                           34

<210> SEQ ID NO 9
<211> LENGTH: 27
<212> TYPE: DNA
<213> ORGANISM: Human

<400> SEQUENCE: 9
aaaaaaaaca tcgcattcct gctggca                                   27

<210> SEQ ID NO 10
<211> LENGTH: 31
<212> TYPE: DNA
<213> ORGANISM: Human
```

<400> SEQUENCE: 10
cccgctcgag tcaggaggtt ttgtcgcagg a        31

<210> SEQ ID NO 11
<211> LENGTH: 19
<212> TYPE: DNA
<213> ORGANISM: Human

<400> SEQUENCE: 11
ggagtgggtc tcatccatt        19

<210> SEQ ID NO 12
<211> LENGTH: 18
<212> TYPE: DNA
<213> ORGANISM: Human

<400> SEQUENCE: 12
gaccttggtg ttgctggg        18

<210> SEQ ID NO 13
<211> LENGTH: 1159
<212> TYPE: DNA
<213> ORGANISM: Escherichia coli

<400> SEQUENCE: 13

```
atataccatg gcgcgccctt tattttcgt gcaaaggaaa acgtttccgc ttatcctttg      60
tgtccggcaa aaacatccct tcagccggag catagagatt aatgactgca ccatcccagg    120
tattaaagat ccgccgccca gacgactggc accttcacct ccgcgatggc gacatgttaa    180
aaactgtcgt gccatatacc agcgaaattt atggacgggc tatcgtaatg cccaatctgg    240
ctccgcccgt gaccaccgtt gaggctgccg tggcgtatcg ccagcgtatt cttgacgccg    300
tacctgccgg gcacgatttc accccattga tgacctgtta tttaacagat tcgctggatc    360
ctaatgagct ggagcgcgga tttaacgaag gcgtgttcac cgctgcaaaa cttacccgg    420
caaacgcaac cactaactcc agccacggcg tgacgtcaat tgacgcaatc atgccggtac    480
ttgagcgcat ggaaaaaatc ggtatgccgc tactggcgca tggtgaagtg acacatgcag    540
atatcgacat ttttgatcgt gaagcgcgct ttatagaaag cgtgatggaa cctctgcgcc    600
agcgcctgac tgcgctgaaa gtcgtttttg agcacatcac caccaaagat gctgccgact    660
atgtccgtga cggaaatgaa cggctggctg ccaccatcac tccgcagcat ctgatgttta    720
accgcaacca tatgctggtt ggaggcgtgc gtccgcacct gtattgtcta cccatcctca    780
aacgtaatat tcaccaacag gcattgcgtg aactggtcgc cagcggtttt aatcgagtat    840
tcctcggtac ggattctgcg ccacatgcac gtcatcgcaa agagagcagt tgcggctgcg    900
cgggctgctt caacgcccca accgcgctgg gcagttacgc taccgtcttt gaagaaatga    960
atgctttgca gcactttgaa gcattctgtt ctgtaaacgg cccgcagttc tatggggttgc   1020
cggtcaacga cacattcatc gaactggtac gtgaagagca acaggttgct gaaagcatcg   1080
cactgactga tgcacgctg gtgccattcc tcgccgggga aacggtacgc tggtccgtta   1140
aacaataacc atggttaac                                                 1159
```